United States Patent [19]

Kolkin et al.

[11] Patent Number: 5,344,410

[45] Date of Patent: Sep. 6, 1994

[54] DEVICE FOR DRAINING THE PLEURAL CAVITY

[76] Inventors: Yakov G. Kolkin, ul.Schorsa, d.25,kv.35, 340050 Donetsk; Vladimir N. Vecherko, bulvar Pushkina, d. 31, kv. 44, 340055 Donetsk; Evgeny S. Pershin, ul.Pogodina, d.23, 340011 Donetsk, all of

[21] Appl. No.: 977,824

[22] Filed: Nov. 17, 1992

[51] Int. Cl.$^5$ .............................................. A61M 5/00
[52] U.S. Cl. ..................... 604/247; 604/122; 604/257; 604/264
[58] Field of Search ................. 604/24, 117, 122, 164, 604/166, 170, 171, 185, 222, 244, 247, 257, 259, 260, 264, 272

[56] References Cited

U.S. PATENT DOCUMENTS

| | | | |
|---|---|---|---|
| 2,700,973 | 2/1955 | Ju | 604/260 |
| 3,074,451 | 1/1963 | Whitney | 604/260 |
| 3,880,311 | 4/1975 | McPhee | 604/260 |
| 4,153,058 | 5/1979 | Nehme | 604/247 |
| 4,813,941 | 3/1989 | Shea | 604/247 |

FOREIGN PATENT DOCUMENTS 1223920 4/1986 U.S.S.R.
1521492 11/1989 U.S.S.R.

Primary Examiner—C. Fred Rosenbaum
Assistant Examiner—N. Kent Gring
Attorney, Agent, or Firm—Collard & Roe

[57] ABSTRACT

The proposed device comprises an outer tube having a central canal and perforations at its one end, a stylet fitted in the central canal of the outer tube, an inner tube, which is in fact a non-return valve and with its one end tightly connected to the outer tube and with its opposite end stretched over the stylet with a possibility of slipping off the latter and getting everted. The device has a receptacle for collecting the pleural fluid, tightly connected to the outer tube and the inner tube, and a retainer for fixing the device in position.

6 Claims, 4 Drawing Sheets

DEVICE FOR DRAINING THE PLEURAL CAVITY

FIELD OF THE INVENTION

The present invention relates generally to medical engineering and, more specifically, to a device for draining the pleural cavity.

The invention can find use for treatment of patients with thoracic injury in case of tension or developing hemopneumothorax.

The herein-proposed device for draining the pleural cavity is applicable in mass destruction foci, that is, when a great many victims are present, especially with the presence of harmful agents (such as toxic agents, pathogens, radioactive substances, and the like) in the external environment.

Furthermore, the present invention is expedient to be applied in any situation wherein time for rendering medical aid is limited, sterilization of the operative field and surgeon's hands is impossible, which is the case with road accident injuries, as well as with accidents in collieries and mines, under field conditions, and so on.

BACKGROUND OF THE INVENTION

One state-of-the-art device for draining the pleural cavity in rendering medical aid to patients with thoracic injury (SU, Patent Application No. 1,521,492) is known to comprise a drainage tube introducible into the pleural cavity by a stylet or mandrin and having a plugged nozzle, a non-return valve for expelling the air from the pleural cavity into the outer atmosphere, and an elastic receptable for accumulating pleural blood.

However, the afore-discussed known device fails to provide tightness of the pleural cavity during its drainage, which is of special importance when the surrounding atmosphere is infected laden with toxic agents, since air is free to penetrate into the pleural cavity as soon as the stylet is removed from the drainage tube introduced into the pleural cavity and until the plug is fitted into drainage tube nozzle.

Another state-of-the-art device for draining the pleural cavity (SU, Patent Application No. 1,223,920) is known to comprise a drainage tube having a central canal and perforations at one of its ends, a non-return valve provided at the opposite tube end, a stylet fitted in the tube central canal, and a retainer of the device shaped as an eyed strip. The device functions as follows. A skin incision is made in, e.g., the sixth intercostal space along the midaxillary line. The drainage tube is introduced, with one of its ends, into the pleural cavity, using a stylet, as far as the strip thrusts against the thoracic wall, whereupon the stylet is withdrawn. Then the non-return valve is fixed at the opposite tube end through a threaded joint.

In the aforesaid device air-tightness of the pleural cavity is disturbed after the stylet is withdrawn from the tube completely and until the non-return valve is fitted at the tube end, with the result that the air from the ambient atmosphere and particles suspended therein are easy to penetrate into the pleural cavity. As a result, the device in question cannot be used in mass destruction foci containing infectious agents, toxic substances, radioactive substances, and the like.

It is an essential object of the present invention to provide air-tightness of the pleural cavity during its draining and a possibility of transportation of a victim, wherein his/her pleural cavity is maintained air-tight.

It is another object of the present invention to cut down the time required for carrying out the procedure of draining the pleural cavity.

It is one more object of the present invention to obviate the danger of infecting the pleural cavity when the proposed device is used in the foci, wherein the ambient atmosphere contains infectious agents, toxic substances, radioactive substances, and the like.

SUMMARY OF THE INVENTION

The foregoing and further objects are accomplished due to the provision of a device for draining the pleural cavity, comprising:

an outer tube having a central canal for the pleural contents to discharge to the surrounding medium;

one end of said outer tube being pointed and having perforations for the pleural contents to get into said central canal;

the opposite end of said outer tube;

a stylet or mandrin fitted movably in said central canal of said outer tube;

one end of said stylet being pointed and extending from said central canal at said one end of said outer tube;

the opposite end of said stylet extending from said central canal at said opposite end of said outer tube;

an inner thin-walled tube made of an elastic material capable of varying its shape, said tube being so tensioned as to slip and evert onto said stylet, thus playing the role of a non-return valve for the pleural gases to escape into the ambient atmosphere;

one end of said inner tube tightly fixed in place on said stylet close to said pointed end thereof;

the opposite end of said inner tube tightly connected to said opposite end of said outer tube;

receptacle for collecting the pleural fluid tightly connected to said opposite end of said outer tube and to said opposite end of said inner tube;

a retainer for fixing the device in position, located on the external surface of said outer tube close to said opposite end thereof.

The fact that the non-return valve is shaped as an inner tube tightly connected to the outer tube and to the receptacle for collecting the pleural fluid, enables a closed air-tight system to be established, which is applicable under any extreme conditions concerned with infecting the surrounding atmosphere. Hermetically sealed interconnection of the device components prevents infection or toxic agents from penetration into the pleural cavity in the course of its drainage and further transportation of the patient.

In addition, provision of the device as a closed system cuts down time required for the drainage procedure, since it dispenses with manipulations involved in connection of the outer tube to the non-return valve and to the receptacle for collecting the pleural fluid.

To facilitate eversion of the inner tube and its slipping off the stylet, it is expedient that said one end of said inner tube be loaded uniformly.

To provide a temporary rigid fixing of the inner tube on the stylet in order to attain air-tightness of the pleural cavity at the instant of piercing the thoracic wall, and easy disengagement of said tube from the stylet, it is desirable that said stylet would have a slot situated nearby said one end thereof. Furthermore, a retainer should be provided for temporary fixing of said one end of said inner tube in said slot of said stylet, said inner tube end being uniformly narrowed. The aforesaid retainer may be shaped as a ring made of elastic material and having a diameter much smaller than the diameter of said stylet.

For more convenient handling and space-saving while in transit the receptacle for collecting the pleural fluid is favourable to be made of an elastic material capable of changing its shape, and said stylet may have a hollow handle adapted to accommodate said receptable for collecting the pleural fluid.

BRIEF DESCRIPTION OF THE DRAWINGS

To promote understanding given below are some specific exemplary embodiments of the present invention to be had with reference to the accompanying drawings, wherein.

DETAILED DESCRIPTION OF THE INVENTION

Figure 1:
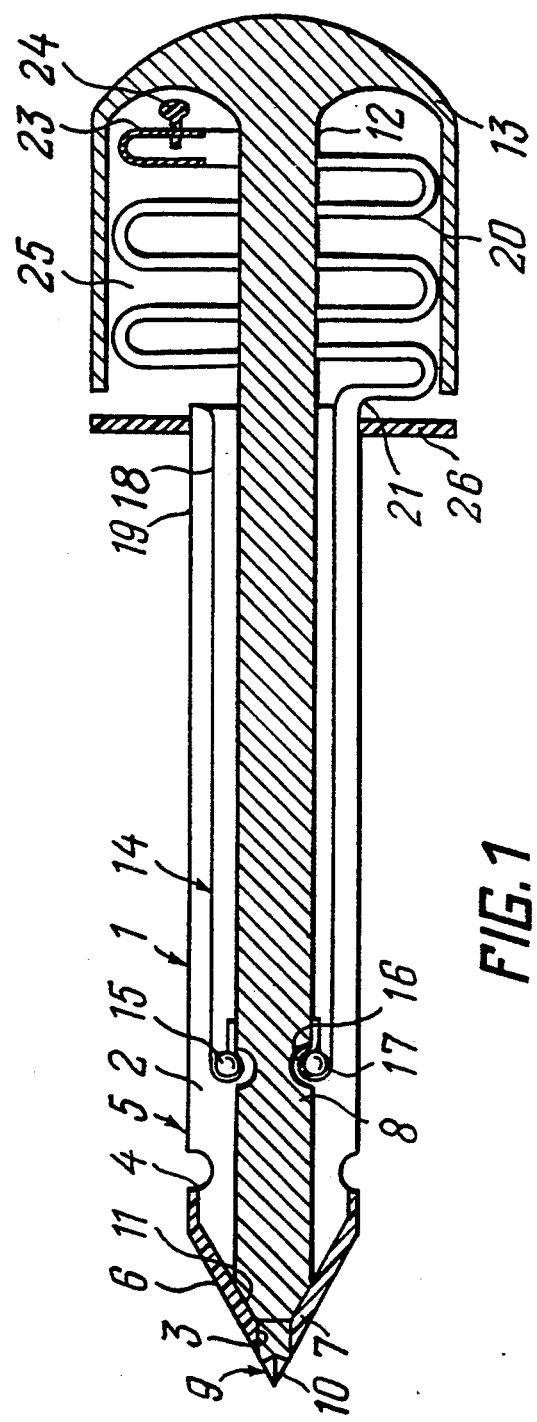
FIG. 1 is a schematic longitudinal sectional view of a device for draining the pleural cavity, according to the invention.

Referring now to FIG. 1 the device for draining the pleural cavity, according to the invention, comprises an outer tube 1 made of an elastic material capable of retaining the original shape, that is, of being not amenable to deformation in the wound canal of the thoracic wall under the action of an elastic force of the surrounding tissues, silicone, latex rubber, or red medical rubber being such a material.

The outer tube 1 has a central canal 2 for discharge of the pleural contents into the ambient medium, and central opening 3, and radial openings 4 provided at an end 5 of the outer tube 1 and adapted for the pleural contents to get to the central canal 2 of the outer tube 1. The end 5 of the outer tube 1 is shaped as a cone frustum 6 having thickened walls 7.

The radial openings 4 provide for discharge of the pleural contents through the central canal 2 of the outer tube 1 when the central opening 3 gets blocked by the lung at the instant of its expansion in the course of drainage.

A stylet 8 is movably fitted in the central canal 2 of the outer tube 1.

An end 9 of the stylet 8 is pointed and has cutting edges 10 extending from the central canal 2 of the outer tube 1, and a supporting platform 11 retaining the outer tube 1 on the stylet 8. A hollow handle 13 is provided at an opposite end 12 of the stylet 8, which can be made of a metal or of any rigid plastics.

An inner tube 14 is stretched over the stylet 8 with a possibility of slipping off and everting, said tube being in fact a non-return valve for the pleural gases to discharge to the ambient atmosphere.

The inner tube 14 is thin-walled and is made of an elastic material capable of varying its shape, such as latex rubber, medical rubber, and the like. Once having been released from the stylet 8 the walls of the inner tue 14, by virtue of their resilience, are capable of moving towards each other under their own weight until getting in full contact with each other, thus establishing a non-return valve which provides for air-tightness of the pleural cavity.

An end 15 of the inner tube 14 is tightly fixed on the stylet 8 close to its pointed end 9. To this aim a slot 16 is provided in the stylet 8 nearby said pointed end 9 thereof, and a retainer is envisaged for temporary fixing of the end 15 of the inner tube 14 on the stylet 8. The retainer is shaped as a rubber ring 17 having a diameter much smaller than the diameter of the stylet 8 and fitted in the slot 16.

According to an alternative embodiment of the present invention, the retainer may be shaped as, e.g., an adhesive layer (omitted in the Drawings) that bonds the end 15 of the inner tube 14 to the stylet 8.

To facilitate everting of the inner tube 14 and its subsequent slipping off the stylet 8, the end 15 of that tube is uniformly narrowed.

An opposite end 18 of the inner tube 14 is tightly connected to an opposite end 19 of the outer tube 1.

Figure 2:
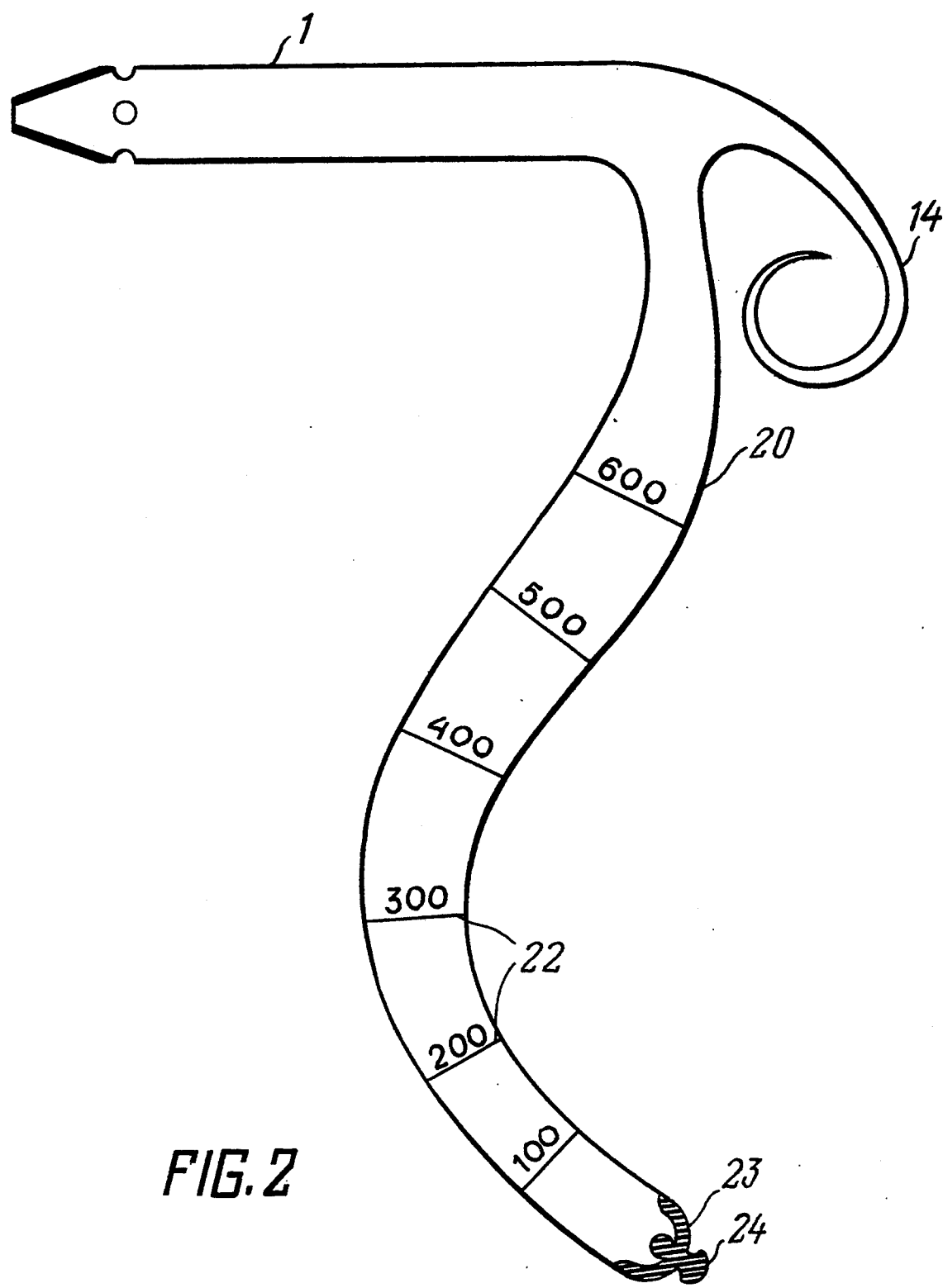
FIG. 2 is a developed view of an air-tight system, incorporating an outer tube, an inner tube, and a receptable for collecting the pleural fluid, according to the invention.

The device of the invention has a receptacle 20 for collecting the pleural fluid, which is thin-walled and made of an elastic material capable of varying its shape (such as latex rubber or medical rubber). The receptacle 20 with its one end 21 is tightly connected to the opposite end 19 of the outer tube 1 and to the opposite end 18 of the inner tube 14 and is provided with numbered graduation marks 22 (FIG. 2) aimed at control of the amount of the pleural fluid discharged. An opposite end 23 (FIG. 1) of the receptacle 20 features a thicker wall, in which an opening is provided to dispose of the accumulated pleural fluid, said opening being closed with a plug 24.

The outer tube 1 (FIG. 2), the inner tube 14, and the receptacle 20 constitute a hermetically sealed closed system and may be made as an integral unit.

To make the proposed device more compact the receptacle 20 (FIG. 1), when folded up, is arranged in a hollow space 25 of the handle 13 of the stylet 8.

A disk 26 is provided nearby the place where the outer tube 1 merges into the inner tube 14 on the external surface of the outer tube 1, said disk limiting further movement of the outer tube 1 into the pleural cavity and serving as retainer of the proposed device.

As an alternative embodiment the fixing disk 26 may be made movable lengthwise the outer tube with a definite force due to friction.

Figure 3:
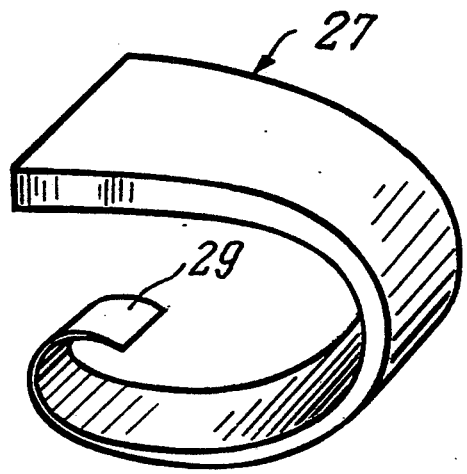
FIG. 3 is an inner tube, according to one embodiment of the invention.
Figure 4:
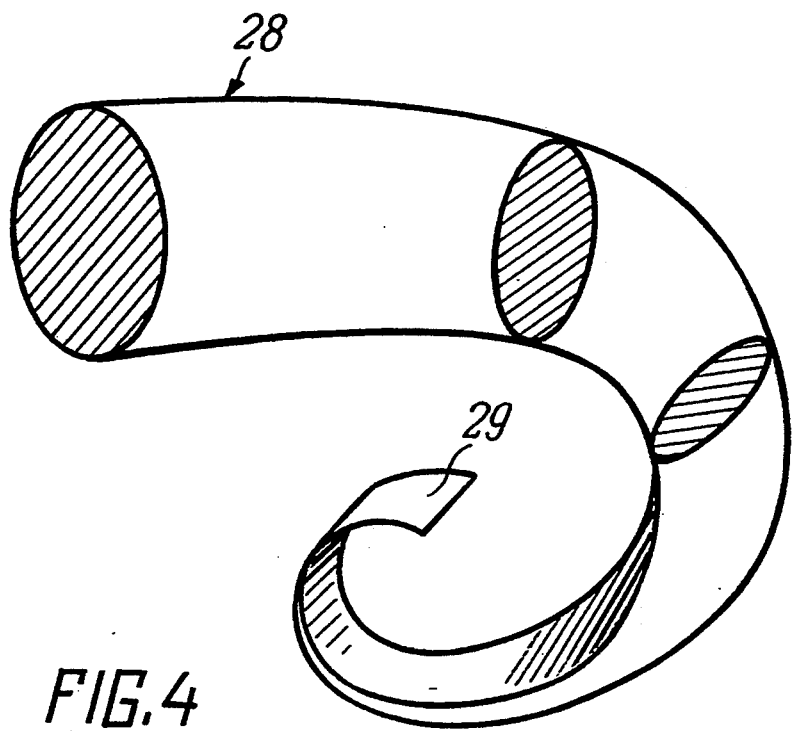
FIG. 4 is another embodiment of the inner tube of FIG. 3.

According to the various embodiments of the proposed device, an inner tube 27 (FIG. 3), 28 (FIG. 4) made as a non-return valve, may have an originally preset shape, e.g., rolled up into a flat spiral and having their walls joined together until a complete contact therebetween as shown in FIG. 3, or the shape of said tube changes toward a free end 29 thereof from tubular to that of a flat band as shown in FIG. 4. In order to retain the originally preset shape of a spiral, to provide its unfolding and separation of its walls when air passes from the pleural cavity into the tube, its walls may be made uniformly thinning towards the free end 29 of the inner tube 27, 28. In addition, the walls of the spiral-shaped tube gradually are brought together towards its free end 29 until getting in an intimate contact with each other.

Figure 5:
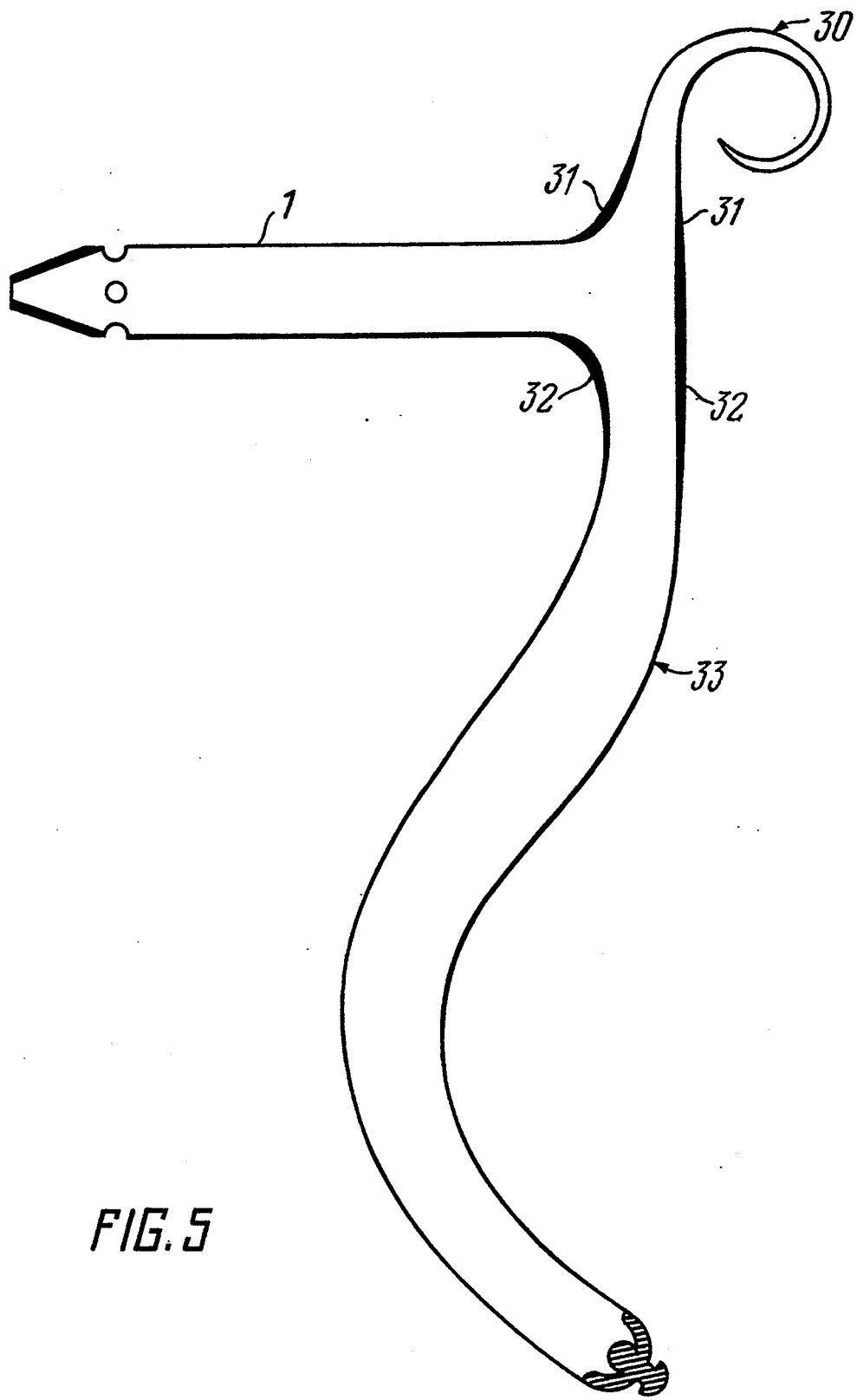
FIG. 5 is one more embodiment of the inner tube of FIG. 3.

To preclude the pleural fluid from penetrating into an inner tube 30 (FIG. 5) its walls 31 may be thickened at the place where the outer tube 1 merges into the inner tube 30 and the latter may be directed upwards, whereas walls 32 of a receptacle 33 for collecting the pleural fluid may be thickened at the place where the outer tube 1 merges into said receptacle and the latter may be directed downwards.

The device for draining the pleural cavity, according to the invention, functions as follows.

A skin incision 0.5–0.7 cm long is made with the aid of a scalpel in, e.g., the second intercostal space along the midclavicular line. Then the device of the invention is introduced into the pleural cavity through said skin incision by virtue of a single motion involving the piercing of the thoracic wall by the pointed end of the device until thrusting against the disk 26 of retainer of said device. Next the stylet 8 is withdrawn along with the inner tube 14 held thereto, which results in that the tube is everted and slips off the stylet 8. Simultaneously the receptacle 20 for collecting the pleural fluid is released from the hollow space 25 of the handle 13 of the stylet 8. In this case the inner tube 14 released from the stylet 8 is in effect a non-return valve rolled up into a spiral. The walls of the valve are brought together, by virtue of their elasticity, until getting in an intimate contact, thus preventing the ambient air from penetrating into the pleural cavity during inspiration or when holding breath, whereby full air-tightness of the pleural cavity is ensured. During subsequent expiration the non-return valve is rolled down by virtue of an excess intrapleural air pressure so that its walls are brought apart, thus promoting the discharge of a next portion of the air.

When ambient air is free to penetrate into the pleural cavity, which is the case with an injury to the lung, the non-return valve functions incessantly, thus preventing the onset of tension pneumothorax. The non-return valve ceases operating automatically as air discontinues to get into the pleural cavity. Blood expelled from the pleural cavity by the respiratory lung excursions runs down by gravity to the receptacle 20, which is in fact a continuous extension to the inner tube 14 and the outer tube 1 to be accumulated therein. The amount of the blood accumulated in the receptacle 20 can easily be measured with the aid of the graduation marks 22 provided on the receptacle wall. When the lung is not injured and the blood is not infected with the ambient air, it can be reinfused whenever necessary.

To keep the device in the pleural cavity after its having been introduced as far as the disk of the retainer and during the draining procedure, the disk is stitched with a ligature that holds the device to the skin.

The proposed device for draining the pleural cavity is compact, is ready for use just after having been withdrawn from the package (e.g., a polyethylene bag or case), and is sterile. The draining procedure is quite simple, since it does away with any manipulations involving the joining of the outer tube with the non-return valve and the receptacle for collecting the pleural fluid. This in turn saves time and prevents the device and the pleural cavity from being infected.

When rendering first aid at the foci of mass destruction with a view to early triage of victims, it is recommendable to mark the proposed devices by colour in order to determine the order of further medical aid at the next stages of casualties evacuation.

The proposed device is expedient to be a part of a surgical emergency kit in emergency aid teams, prompt-response parties, civil defense medical officers, and the like services.

The device of the invention makes it possible to:

maintain natural air-tightness of the pleural cavity in the case of an intact lung, thus preventing the onset of pneumothorax in the course of drainage of the pleural cavity, as well as the penetration of infectious agents together with the ambient air, toxic substances, and other noxious agents;

dispense with manipulations concerned with connection of the outer tube to the non-return valve and the receptacle for collecting the pleural fluid in cases of rendering emergency aid to the patient, especially under field conditions, which cuts down much the time for the draining procedure;

to promptly eliminate tension hemopneumothorax in the case of an injured lung or bronchus.

What is claimed is:

1. A device for draining pleural contents from the pleural cavity comprising:
    an outer tube having a hollow interior, a proximal end with perforations and a distal end;
    an elastic inner tube, removably disposed within said outer tube and having a proximal end and a distal end connected to said outer tube distal end;
    a stylet, removably disposed within said inner tube and having a pointed end, extending outwardly from the proximal end of said outer tube, adapted for guiding the device into the pleural cavity; said proximal end of said inner tube is tightly, elastically connected to said stylet near its pointed end;
    a pleural contents receptacle connected to said distal ends of said outer tube and said inner tube and being in communication with the hollow interior of said outer tube;
    a retaining collar connected to said outer tube near said distal end for retaining the device in position; and
    wherein removal of said stylet everting said inner tube and forming an airtight seal, whereby the pleural contents flowing from the pleural cavity through the perforations and the hollow interior into said pleural contents receptacle.

2. The device according to claim 1, wherein said inner tube uniformly narrows from its distal end to its proximal end.

3. The device according to claim 2, further comprising a retaining member;
    wherein said stylet includes a slot near its pointed end and said retaining member removably connects said inner tube to said stylet slot.

4. The device according to claim 3, wherein said retaining member is an elastic ring having a diameter smaller than a diameter of said stylet.

5. The device according to claim 4, wherein said pleural contents receptacle is made of an elastic material.

6. The device according to claim 5, wherein said stylet includes a hollow handle opposite said pointed end for storing said pleural contents receptacle therein prior to use.

* * * * *